(12) United States Patent
Liang et al.

(10) Patent No.: US 11,597,714 B2
(45) Date of Patent: Mar. 7, 2023

(54) PLEUROMULIN LIPOIC ACID ESTER WITH ANTIBACTERIAL ACTIVITY AND A METHOD OF PREPARING THE SAME

(71) Applicants: Chengyuan Liang, Xi+3 an (CN); Cong Du, Xi+3 an (CN); Qianqian Zhao, Xi+3 an (CN); Liang Xin, Xi+3 an (CN); Jingyi Li, Xi+3 an (CN); Dan Yang, Xi+3 an (CN); Nan Hui, Xi+3 an (CN); Guaiping Qiao, Xi+3 an (CN); Han Li, Xi+3 an (CN); Yanjun Li, Xi+3 an (CN); Liang Qi, Xi+3 an (CN); Wenbo Yao, Xi+3 an (CN); Gennian Mao, Xi'an (CN)

(72) Inventors: Chengyuan Liang, Xi+3 an (CN); Cong Du, Xi+3 an (CN); Qianqian Zhao, Xi+3 an (CN); Liang Xin, Xi+3 an (CN); Jingyi Li, Xi+3 an (CN); Dan Yang, Xi+3 an (CN); Nan Hui, Xi+3 an (CN); Guaiping Qiao, Xi+3 an (CN); Han Li, Xi+3 an (CN); Yanjun Li, Xi+3 an (CN); Liang Qi, Xi+3 an (CN); Wenbo Yao, Xi+3 an (CN); Gennian Mao, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 183 days.

(21) Appl. No.: 17/128,103

(22) Filed: Dec. 19, 2020

(65) Prior Publication Data

US 2022/0194918 A1 Jun. 23, 2022

(51) Int. Cl.
*C07D 339/04* (2006.01)
*A61P 31/04* (2006.01)

(52) U.S. Cl.
CPC ............ *C07D 339/04* (2013.01); *A61P 31/04* (2018.01)

(58) Field of Classification Search
CPC ............................... C07D 339/04; A61P 31/04
See application file for complete search history.

*Primary Examiner* — John S Kenyon

(57) ABSTRACT

A compound with anti-drug resistant bacteria activity having the following formula (I):

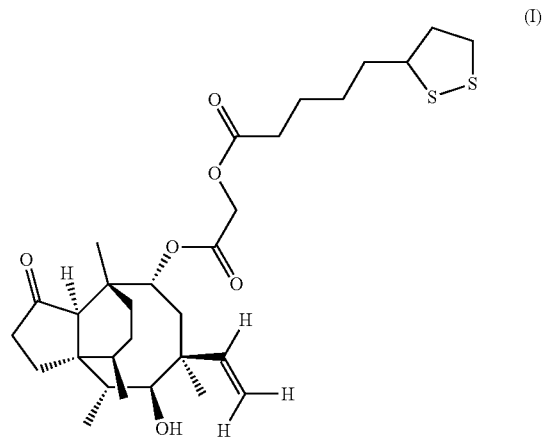

is disclosed. A method of preparing the compound of formula (I) is also disclosed.

16 Claims, 2 Drawing Sheets

PLEUROMULIN LIPOIC ACID ESTER WITH ANTIBACTERIAL ACTIVITY AND A METHOD OF PREPARING THE SAME

FIELD OF THE INVENTION

The present invention relates to the field of medicinal chemistry, and in particular, to a pleuromulin lipoic acid ester with antibacterial activity and a method of preparing the same.

BACKGROUND OF THE INVENTION

Multi-drug resistant bacteria (MDR) infections are now spread all over the world, and can cause sporadic, cross-spread, and even outbreaks in communities or hospitals. It is particularly threatening to infants and young children, immunocompromised persons and the elderly. Since most of the commonly used antibacterial drugs (most β-lactams, aminoglycosides, fluoroquinolones, macrolides, tetracyclines, etc.) used for MDR infections do not work well, clinical treatment has become a difficult problem. While making good use of existing antibacterial drugs, we should also develop new antibacterial drugs that are low in toxicity and effective in controlling MDR.

Pleuromulin is an antibiotic produced by submerged culture of the higher fungi basidiomycetes pleurots mutilus and plenrots passeckerianus, and belongs to diterpenoids. The main skeleton is composed of five-membered six-membered and eight-membered rings. Pleuromulin and its derivatives can inhibit the synthesis of bacterial protein at the ribosome level, and have a unique effect on many Gram-positive bacteria and Mycoplasma infections.

Lipoic acid belongs to a class of compounds in the B vitamins. It is an important coenzyme in the organism and one of the indispensable substances in the tricarboxylic acid cycle. In addition to acting as a coenzyme, lipoic acid also has a powerful antioxidant function, which can eliminate free radicals that cause accelerated aging and disease. It has multiple functions such as anti-oxidation, anti-aging, improving immunity, preventing cardiovascular diseases, and relieving symptoms of diabetes.

In the present invention, pleuromulin is modified by lipoic acid to obtain a pleuromulin lipoic acid ester. The preliminary antibacterial activity experiment shows that the compound has excellent antibacterial activity and has high medical research and application value in the treatment of infectious diseases caused by multidrug resistant bacteria.

SUMMARY OF THE INVENTION

In one embodiment, the present invention provides a pleuromulin lipoic acid ester, i.e., a compound having the following formula (I):

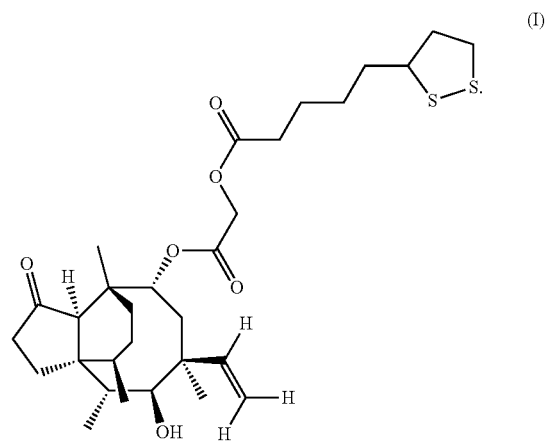 [SMILES: C=C[C@]1(C)C[C@@H](OC(=O)COC(=O)CCCCC2CCSS2)[C@]2(C)CC[C@@H](C)[C@@]3(CCC(=O)[C@@H]23)[C@@H](C)[C@@H]1O]

In another embodiment, the present application provides a method of preparing the compound of formula (I). The method includes: reacting a compound of formula (II) (pleuromulin) with a compound of formula (III) (lipoic acid) to obtain the compound of formula (I):

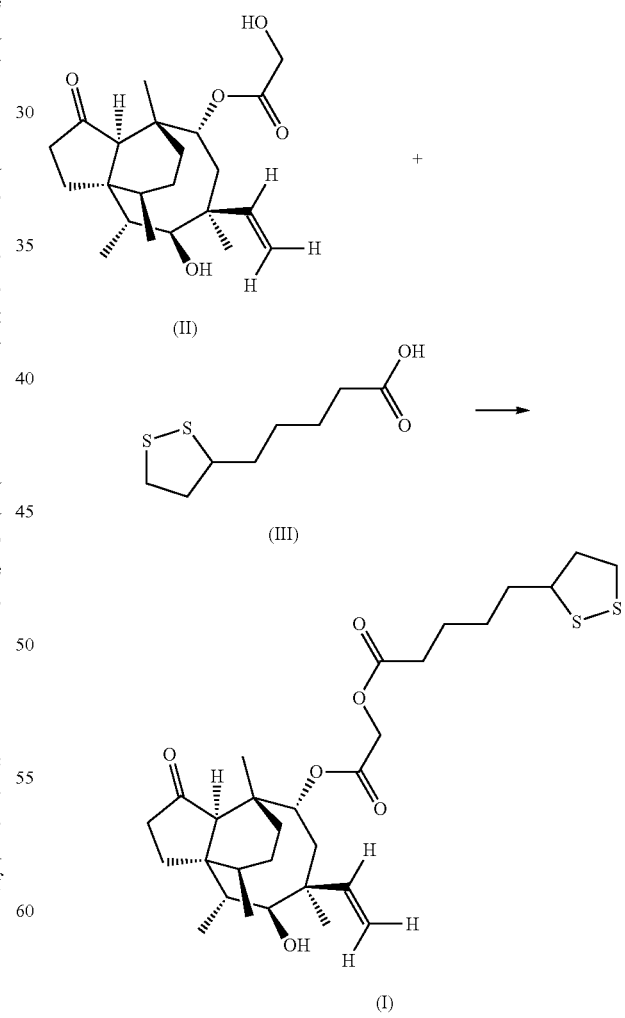

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent, a catalytic amount of 4-DMAP ((4-dimethylamino)pyridine), and DCC (N,N'-Dicyclohexylcarbodiimide) under nitrogen atmosphere to obtain a reaction mixture; heating the reaction mixture at 20-40° C. for 8-12 hours; and concentrating the reaction mixture and extracting with ethyl acetate to obtain a crude product; and purifying the crude product on a silica gel fresh chromatography column with dichloromethane and methanol as an eluent to obtain the compound of formula (I).

In another embodiment, the organic solvent is toluene, dichloromethane or DMF (dimethylformamide).

In another embodiment, the organic solvent is dichloromethane.

In another embodiment, the molar ratio of the compound of formula (II) and the compound of formula (III) is 1:1.2.

In another embodiment, the reaction mixture is heated at 25° C.

In another embodiment, the reaction mixture is heated for 10 hours.

In another embodiment, the eluent is dichloromethane:methanol=20:1.

In another embodiment, the reaction of the compound of formula (II) with the compound of formula (III) includes the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 10-50° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-ethyl-3-methylimidazolium tetrachloroferrate,1-octyl-3-methylimidazolium hexafluorophosphate, or 1-butyl-3-methylimidazolium tetrafluoroborate.

In another embodiment, the ionic liquid is 1-octyl-3-methylimidazolium hexafluorophosphate ($C_{12}H_{23}F_6N_2P$).

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 20° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
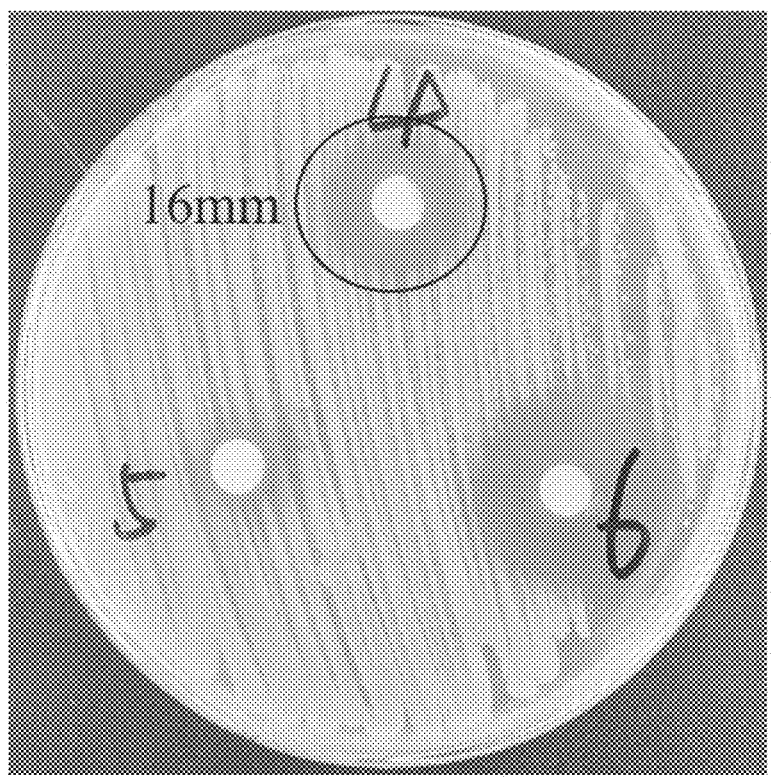
FIG. 1 shows the antibacterial effect of the pleuromulin lipoic acid ester on multi-resistant *Staphylococcus aureus* 18-206.

Reference will now be made in detail to embodiments of the present invention, example of which is illustrated in the accompanying drawings. The following examples illustrate the present invention, but the present invention is not limited to the following examples.

Example 1

Preparation of the pleuromulin lipoic acid ester (2-(((3aS,4R,5S,6S,8R,9R,9aR,12R)-5-hydroxy-4,6,9,12-tetramethyl-1-oxo-6-vinyldecahydro-3a, 9-propanocyclopenta[8]annulen-8-yl)oxy)-2-oxoethyl 5-(1,2-dithiolan-3-yl)pentanoate)

In a 100 mL three-necked flask, 75.7 mg (0.20 mmol) of pleuromutilin, 49.5 mg (0.24 mmol) lipoic acid and 2.4 mg (0.02 mmol) 4-DMAP (4-dimethylamino)pyridine were dissolved in 20 mL dichloromethane. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 25° C. for 10 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 85.5 mg of the pleuromulin lipoic acid ester, a total yield of 75.49%.

$^1$H-NMR (400 MHz, chloroform-d) δ (ppm): 6.51(1H, m), 5.84 (1H, d), 5.34 (2H, s), 4.58 (1H, d), 3.61(1H, t), 3.40 (1H, s), 3.21 (1H, d), 2.54 (1H, m), 2.47 (2H, t), 2.35 (2H, t), 2.25 (1H, s), 2.00-1.91 (6H, m), 1.72 (2H, m), 1.62-1.50 (8H, m), 1.48 (2H, m), 1.43 (3H, m), 1.22 (2H, m), 1.17 (3H, m), 0.93 (3H, d), 0.80 (3H, d); $^{13}$C-NMR (400 MHz, chloroform-d) δ (ppm): 216.8, 172.6, 166.7, 138.8, 117.3, 74.6, 69.6, 61.2, 58.0, 56.3, 45.4, 44.6, 44.0, 41.9, 40.2, 38.5, 36.0, 34.5, 33.5, 30.4, 28.6, 26.5, 24.8, 24.5, 16.6, 14.8, 11.4.

Example 2

Preparation of the pleuromulin lipoic acid ester

In a 100 mL three-necked flask, 75.7 mg (0.20 mmol) of pleuromutilin, 49.5 mg (0.24 mmol) lipoic acid and 2.4 mg (0.02 mmol) 4-DMAP (4-dimethylamino)pyridine were dissolved in 20 mL toluene. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 20° C. for 12 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 72.9 mg of the pleuromulin lipoic acid ester, a total yield of 64.35%.

Example 3
Preparation of the pleuromulin lipoic acid ester
In a 100 mL three-necked flask, 75.7 mg (0.20 mmol) of pleuromutilin, 45.4 mg (0.24 mmol) lipoic acid and 2.4 mg (0.02 mmol) 4-DMAP (4-dimethylamino)pyridine were dissolved in 20 mL DMF. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 30° C. for 10 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 76.1 mg of the pleuromulin lipoic acid ester, a total yield of 67.19%.

Example 4
Preparation of the pleuromulin lipoic acid ester
In a 100 mL three-necked flask, 75.7 mg (0.20 mmol) of pleuromutilin, 45.4 mg (0.22 mmol) lipoic acid and 2.4 mg (0.02 mmol) 4-DMAP (4-dimethylamino)pyridine were dissolved in 20 mL dichloromethane. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 35° C. for 8 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 78.4 mg of the pleuromulin lipoic acid ester, a total yield of 69.25%.

Example 5
Preparation of the pleuromulin lipoic acid ester
In a 100 mL three-necked flask, 75.7 mg (0.20 mmol) of pleuromutilin, 49.5 mg (0.24 mmol) lipoic acid and 2.4 mg (0.02 mmol) 4-DMAP (4-dimethylamino)pyridine were dissolved in 20 mL toluene. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 40° C. for 8 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 71.8 mg of the pleuromulin lipoic acid ester, a total yield of 63.41%.

Example 6
Preparation of the pleuromulin lipoic acid ester
In a 100 mL three-necked flask, 75.7 mg (0.20 mmol) of pleuromutilin, 53.6 mg (0.26 mmol) lipoic acid and 2.4 mg (0.02 mmol) 4-DMAP (4-dimethylamino)pyridine were dissolved in 20 mL DMF. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 20° C. for 9 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 75.2 mg of the pleuromulin lipoic acid ester, a total yield of 66.41%.

Example 7
Preparation of the pleuromulin lipoic acid ester
In a 100 mL three-necked flask, 75.7 mg (0.20 mmol) of pleuromutilin, 47.5 mg (0.23 mmol) lipoic acid and 2.4 mg (0.02 mmol) 4-DMAP (4-dimethylamino)pyridine were dissolved in 20 mL dichloromethane. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 35° C. for 9 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 79.9 mg of the pleuromulin lipoic acid ester, a total yield of 70.56%.

Example 8
Preparation of the pleuromulin lipoic acid ester
In a 100 mL three-necked flask, 75.7 mg (0.20 mmol) of pleuromutilin, 47.5 mg (0.23 mmol) lipoic acid and 2.4 mg (0.02 mmol) 4-DMAP (4-dimethylamino)pyridine were dissolved in 20 mL toluene. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 30° C. for 11 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 71.3 mg of the pleuromulin lipoic acid ester, a total yield of 62.95%.

Example 9
Preparation of the pleuromulin lipoic acid ester
In a 100 mL three-necked flask, 75.7 mg (0.20 mmol) of pleuromutilin, 47.5 mg (0.23 mmol) lipoic acid and 2.4 mg (0.02 mmol) 4-DMAP (4-dimethylamino)pyridine were dissolved in 20 mL DMF. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 40° C. for 11 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 76.3 mg of the pleuromulin lipoic acid ester, a total yield of 67.41%.

Example 10
Preparation of the pleuromulin lipoic acid ester

In a 100 mL three-necked flask, 75.7 mg (0.20 mmol) of pleuromutilin, 53.6 mg (0.26 mmol) lipoic acid and 2.4 mg (0.02 mmol) 4-DMAP (4-dimethylamino)pyridine were dissolved in 20 mL dichloromethane. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 20° C. for 12 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol=20:1 as eluent, and the eluent containing the product was combined, concentrated under reduced pressure, and dried to obtain 81.6 mg of the pleuromulin lipoic acid ester, a total yield of 72.05%.

Example 11
Preparation of the pleuromulin lipoic acid ester

In a 100 mL three-necked flask, 75.7 mg (0.20 mmol) of pleuromutilin, 49.5 mg (0.24 mmol) lipoic acid and 2.4 mg (0.02 mmol) 4-DMAP (4-dimethylamino)pyridine were dissolved in 20 mL dichloromethane. After stirring for five minutes at 0° C., 41.2 mg (0.20 mmol) of condensing agent DCC (N,N'-Dicyclohexylcarbodiimide) was added under nitrogen atmosphere. The reaction mixture was stirred at 30° C. for 11 hours. Thin layer chromatography was used to track the reaction to completion, heating was stopped, and the protective device was removed. The reaction mixture was washed with water, extracted with ethyl acetate, concentrated and dried to give a crude product. The crude product was purified by silica gel column chromatography, with dichloromethane: methanol =20:1 as eluent, and the eluent containing the product was combined, concentrated under reduced pressure, and dried to obtain 79.5 mg of the pleuromulin lipoic acid ester, a total yield of 70.16%.

Example 12
Preparation of the pleuromulin lipoic acid ester

In a 100 mL three-necked flask, 75.7 mg (0.20 mmol) of pleuromutilin, 45.4 mg (0.22 mmol) of lipoic acid and 3.7 mg (0.002 mmol) silicomolybdic acid were dissolved in 30 mL of 1-octyl-3-methylimidazolium hexafluorophosphate under nitrogen atmosphere. After full dissolution, the reaction mixture was stirred at 20° C. for 6 hours. Thin layer chromatography was used to track the reaction to completion, heating was stopped, and the protective device was removed. The reaction mixture was allowed to separate into layers to give a crude product. The crude product was recrystallized with 10 mL methanol and dried to obtain 96.0 mg of the pleuromulin lipoic acid ester, a total yield of 84.79%.

Example 13
Preparation of the pleuromulin lipoic acid ester

In a 100 mL three-necked flask, 75.7 mg (0.20 mmol) of pleuromutilin, 45.4 mg (0.22 mmol) of lipoic acid and 3.7 mg (0.002 mmol) silicomolybdic acid were dissolved in 30 mL of 1-ethyl-3-methylimidazolium tetrachloroferrate under nitrogen atmosphere. After full dissolution, the reaction mixture was stirred at 10° C. for 8 hours. Thin layer chromatography was used to track the reaction to completion, and the protective device was removed. The reaction mixture was allowed to separate into layers to give a crude product. The crude product was recrystallized with 10 mL methanol and dried to obtain 90.5 mg of the pleuromulin lipoic acid ester, a total yield of 79.959%.

Example 14
Preparation of the pleuromulin lipoic acid ester

In a 100 mL three-necked flask, 75.7 mg (0.20 mmol) of pleuromutilin, 45.4 mg (0.22 mmol) of lipoic acid and 3.7 mg (0.002 mmol) silicomolybdic acid were dissolved in 30 mL of 1-butyl-3-methylimidazolium tetrafluoroborate under nitrogen atmosphere. After full dissolution, the reaction mixture was stirred at 50° C. for 4 hours. Thin layer chromatography was used to track the reaction to completion, heating was stopped, and the protective device was removed. The reaction mixture was allowed to separate into layers to give a crude product. The crude product was recrystallized with 10 mL methanol and dried to obtain 92.2 mg of the pleuromulin lipoic acid ester, a total yield of 81.43%.

Example 15
Preparation of the pleuromulin lipoic acid ester

In a 100 mL three-necked flask, 75.7 mg (0.20 mmol) of pleuromutilin, 45.4 mg (0.22 mmol) of lipoic acid and 3.7 mg (0.002 mmol) silicomolybdic acid were dissolved in 30 mL of 1-octyl-3-methylimidazolium hexafluorophosphate under nitrogen atmosphere. After full dissolution, the reaction mixture was stirred at 20° C. for 8 hours. Thin layer chromatography was used to track the reaction to completion, heating was stopped, and the protective device was removed. The reaction mixture was allowed to separate into layers to give a crude product. The crude product was recrystallized with 10 mL methanol and dried to obtain 92.9 mg of the pleuromulin lipoic acid ester, a total yield of 82.07%.

Example 16
Antibacterial activity test of the compounds of the invention

The antimicrobial efficacy was determined by a paper diffusion drug sensitivity test.

Experimental strains: multi-resistant *Staphylococcus aureus* 18-206, multi-resistant *Staphylococcus aureus* 18-222, multi-resistant *Staphylococcus aureus* 18-596. The experimental strain was identified by Huashan Hospital Affiliated to Fudan University (Institute of Antibiotic of Fudan University).

Drug sensitive paper: The drug sensitive paper is a special drug sensitive paper with a diameter of 6.35 mm and a water absorption of 0.02 mL. The control drug was vancomycin (30 μg/tablet); the test drugs were pleuromulin (30 μg/tablet), lipoic acid (30 μg/tablet) and pleuromulin lipoic acid ester (30 μg/tablet).

Reagents: LB agar medium, LA broth medium, 0.5% DMSO solution.

Equipment: Ultra-clean workbench, high-pressure sterilization pot, gas bath constant temperature shaking incubator.

Preparation of bacterial suspension:

The experimental strains were inoculated in non-selective medium and placed in air at 37° C. for 24 h. Pick a single colony that grows well and inoculate it into broth medium, incubate at 35° C.±2° C. for 6 hours, and use LA broth medium to calibrate the concentration of the bacterial solution to 0.5 Mie turbidimetric tube ($1.5 \times 10^8$ CFU/mL). A bacterial suspension is obtained.

Paper diffusion method drug sensitivity test:

Weigh the LB dry powder, sterilize at 103.4 Kpa, 121.3° C. high-pressure steam for 15 min, and then put it in a 40° C.-50° C. water bath. Place a sterile empty plate (inner diameter 9 cm) on the surface of the ultra-clean table water table, shake and shake LB, and then pour the plate. The thickness of each plate is 3 mm to 4 mm. After the plate is cooled at room temperature, store it in the refrigerator at 2° C.-8° C. Use a sterile cotton swab to dip the bacterial solution, and evenly coat the surface of the LB plate 3 times. After inoculation of the bacterial suspension, the LB plate was dried at room temperature for 3 min to 5 min. Use sterile forceps to closely attach the antibacterial drug paper to the dish. Put the dish upside down and place it in a 37° C. incubator for 24 h. Observe the result and measure the diameter. Taking 0.5% DMSO solution as a negative control, the antibacterial activity is expressed by the diameter of the inhibition zone. The inhibition zone 17 mm, sensitive; the inhibition zone is 15 mm-16 mm, intermediary; the inhibition zone 14 mm, drug resistance.

Figure 2:
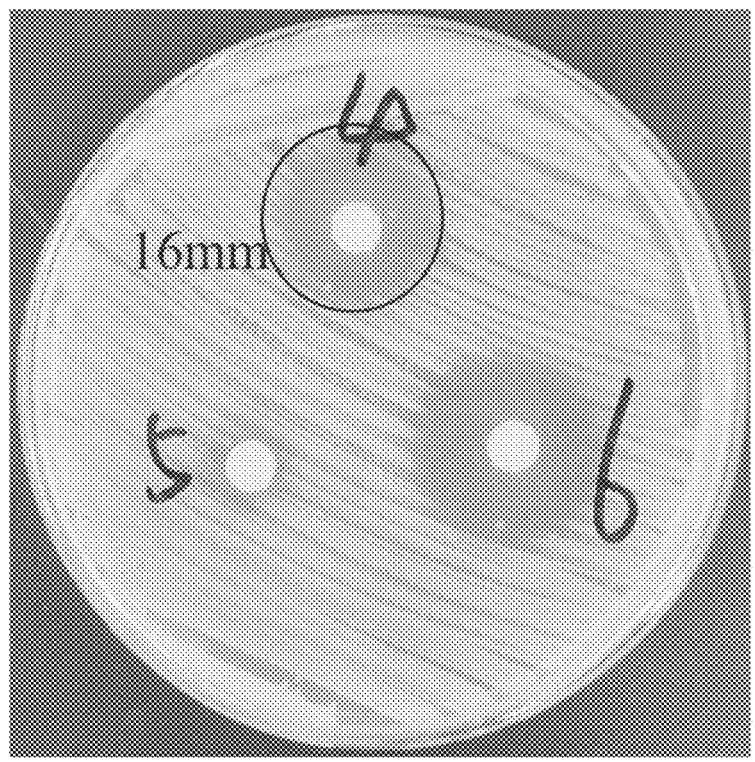
FIG. 2 shows the antibacterial effect of the pleuromulin lipoic acid ester on multi-resistant *Staphylococcus aureus* 18-222.
Figure 3:
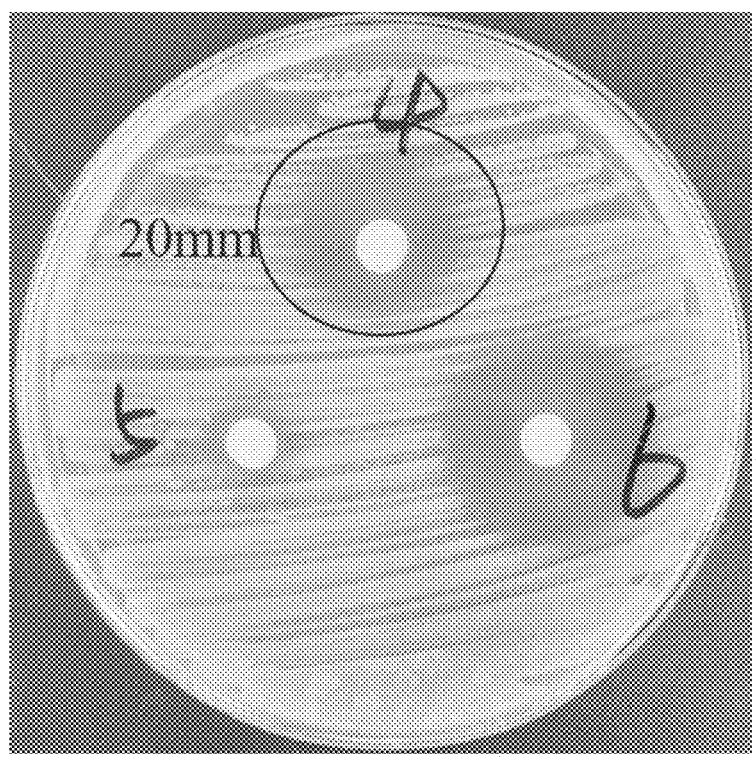
FIG. 3 shows the antibacterial effect of the pleuromulin lipoic acid ester on multi-resistant *Staphylococcus aureus* 18-596.

In FIGS. 1-3, the pleuromulin lipoic acid ester is represented by the number six. FIG. 1 shows the antibacterial effect of the pleuromulin lipoic acid ester on multi-resistant *Staphylococcus aureus* 18-206. FIG. 2 shows the antibacterial effect of the pleuromulin lipoic acid ester on multi-resistant *Staphylococcus aureus* 18-222. FIG. 3 shows the antibacterial effect of the pleuromulin lipoic acid ester on multi-resistant *Staphylococcus aureus* 18-596. The results are shown in Table 1.

TABLE 1

Experimental results of the zone of inhibition

| Compound | Zone of inhibition/mm Strain | | |
|---|---|---|---|
| | Multi-resistant *Staphylococcus aureus* 18-206 | Multi-resistant *Staphylococcus aureus* 18-222 | Multi-resistant *Staphylococcus aureus* 18-596 |
| 0.5% DMSO | 0 | 0 | 0 |
| Vancomycin | 17 | 18 | 21 |
| Pleuromulin | 0 | 0 | 0 |
| Lipoic acid | 0 | 0 | 0 |
| Pleuromulin lipoic acid ester | 16 | 16 | 20 |

The results in FIGS. 1-3 and Table 1 show that the starting materials pleuromutilin and lipoic acid have no inhibitory effect on drug-resistant bacteria. Pleuromutilin lipoic acid ester has strong inhibitory effects on multi-drug resistant *Staphylococcus aureus* 18-206, 18-222, 18-596, and the diameter of bacteriostatic zone against multidrug resistant *Staphylococcus aureus* 18-596 was up to 21 mm. In summary, the pleuromutilin lipoic acid ester of the present invention can be used as an antibacterial drug candidate for multi-drug resistant *Staphylococcus aureus*, and further preclinical studies will be conducted.

What is claimed is:

1. A compound having the following formula (I):

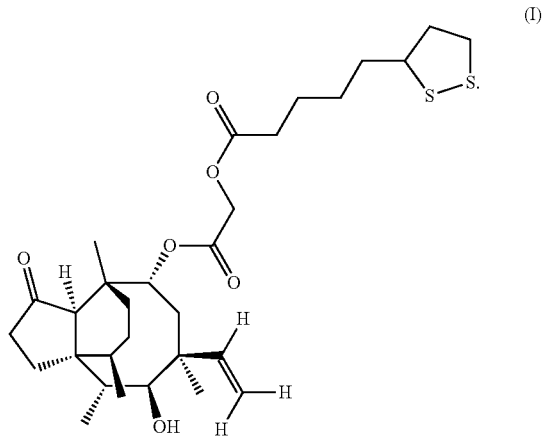 [SMILES: C=C[C@]1(C)C[C@@H](OC(=O)COC(=O)CCCCC2CCSS2)[C@]2(C)CC[C@@H](C)[C@@]3(CCC(=O)[C@@H]23)[C@@H](C)[C@@H]1O]

(I)

2. A method of preparing the compound of formula (I) of claim 1, comprising: reacting a compound of formula (II) with a compound of formula (III) to obtain the compound of formula (I):

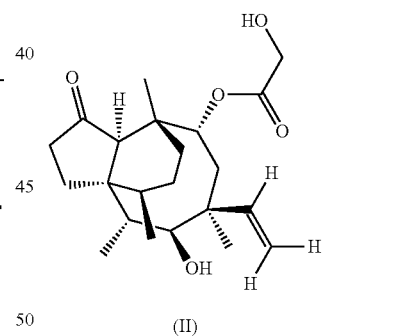

(II)

+

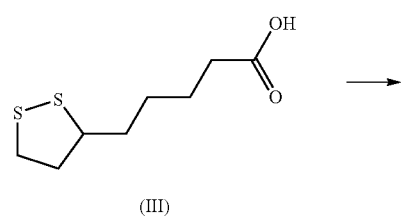

(III)

-continued

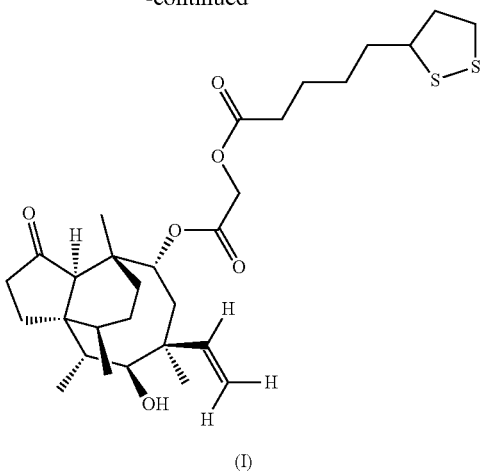

(I)

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent, a catalytic amount of 4-DMAP ((4-dimethylamino)pyridine), and DCC (N,N'-Dicyclohexylcarbodiimide) under nitrogen atmosphere to obtain a reaction mixture;
heating the reaction mixture at 20-40° C. for 8-12 hours; and
concentrating the reaction mixture and extracting with ethyl acetate to obtain a crude product; and
purifying the crude product on a silica gel fresh chromatography column with dichloromethane and methanol as an eluent to obtain the compound of formula (I).

4. The method of claim 3, wherein the organic solvent is toluene, dichloromethane or DMF (dimethylformamide).

5. The method of claim 4, wherein the organic solvent is dichloromethane.

6. The method of claim 3, wherein the molar ratio of the compound of formula (II) and the compound of formula (III) is 1:1.2.

7. The method of claim 3, wherein the reaction mixture is heated at 25° C.

8. The method of claim 3, wherein the reaction mixture is heated for 10 hours.

9. The method of claim 3, wherein the eluent is dichloromethane: methanol=20:1.

10. The method of claim 2, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 10-50° C. for 4-8 hours;
placing the reaction mixture in a separating funnel to separate a crude product;
purifying the crude product by recrystallization in methanol to obtain the compound of formula (I); and
recycling the ionic liquid.

11. The method of claim 10, wherein the ionic liquid is 1-ethyl-3-methylimidazo-lium tetrachloroferrate, 1-octyl-3-methylimidazolium hexafluorophosphate, or 1-butyl-3-methylimidazolium tetrafluoroborate.

12. The method of claim 11, wherein the ionic liquid is 1-octyl-3-methylimidazolium hexafluorophosphate.

13. The method of claim 10, wherein the compound of formula (II) and the compound (III) have a molar ratio of 1:1 to 1:1.3.

14. The method of claim 13, wherein the molar ratio of the compound of formula (II) and the compound of formula (III) is 1:1.1.

15. The method of claim 10, wherein the reaction mixture is heated at 20° C.

16. The method of claim 10, wherein the reaction mixture is heated for 6 hours.

* * * * *